United States Patent
Andrews et al.

(10) Patent No.: US 10,438,149 B2
(45) Date of Patent: *Oct. 8, 2019

(54) HEALTHCARE DELIVERY VERIFICATION SYSTEM

(71) Applicant: Kinnser Software, Inc., Austin, TX (US)

(72) Inventors: Kris Andrews, Austin, TX (US);
Arnold Cano, Austin, TX (US);
Edmund Danyal, Austin, TX (US);
Michael Ditson, Austin, TX (US);
Christopher Hester, Austin, TX (US);
Richard Mueller, Austin, TX (US);
Julie Olivier, Cedar Creek, TX (US);
George Santillan, Austin, TX (US)

(73) Assignee: Wellsky Home Health & Hospice Corporation, Austin, TX (US)

( * ) Notice: Subject to any disclaimer, the term of this patent is extended or adjusted under 35 U.S.C. 154(b) by 643 days.

This patent is subject to a terminal disclaimer.

(21) Appl. No.: 15/272,325

(22) Filed: Sep. 21, 2016

(65) Prior Publication Data

US 2017/0011180 A1    Jan. 12, 2017

Related U.S. Application Data

(63) Continuation of application No. 14/205,257, filed on Mar. 11, 2014, now Pat. No. 9,471,749.

(60) Provisional application No. 61/783,913, filed on Mar. 14, 2013.

(51) Int. Cl.
*G06Q 10/06* (2012.01)
*G06F 19/00* (2018.01)
*G16H 40/20* (2018.01)

(52) U.S. Cl.
CPC ... *G06Q 10/063114* (2013.01); *G06F 19/328* (2013.01); *G16H 40/20* (2018.01)

(58) Field of Classification Search
CPC ............ G06Q 10/063114; G16H 40/20; G06F 19/328
See application file for complete search history.

(56) References Cited

U.S. PATENT DOCUMENTS

2013/0090939 A1*   4/2013   Robinson ............... G06Q 50/22
                                                             705/2

* cited by examiner

*Primary Examiner* — Linh Giang Le
(74) *Attorney, Agent, or Firm* — The Ruble Law Firm, P.C.; Richard R. Ruble, Esq.

(57) ABSTRACT

The present disclosure describes a system, method and computer readable medium capable of verifying healthcare encounters. In one embodiment, an electronic verification process is described which may utilize geographical information to determine the proximity of a health care worker to the patient during a scheduled healthcare visit. The proximity information may then be compared to a threshold value and an electronic signature screen may be presented to the patient based upon the results of the comparison. In one embodiment, a time stamp may be generated and stored to provide confirmation as to the time that the patient's electronic signature was obtained via the electronic signature screen. Verification information stored by the system may be used to simplify the verification process, hasten payments to healthcare organizations and protect against healthcare fraud.

20 Claims, 4 Drawing Sheets

| iPad 🛜 | | | 2:27 PM | | | 7% |
|---|---|---|---|---|---|---|
| ✕ | ◁ ▷ ⬜ ⬆ | kinnser.net/am/hotbox.cfm | | ⟳ | SEARCH | + |
| | | HOTBOX \| KINNSER SOFTWARE | | | | |
| GO TO FILE SEARCH HELP | | | | | RESET FILTER HELP ⬆ | |

HOTBOX

BRANCH [ALL ▽]  VISITS IN ITALICS HAVE BEEN ADDED OR EDITED WITHIN THE PAST 48 HOURS.
TASKS [ALL ▽]  VISITS IN RED OCCURRED IN EPISODES THAT HAVE ALREADY ENDED.

ALL BRANCHES, ALL TASK TYPES

SHOW [25 ▽] ENTRIES  GROUPED BY [DATE ▽]  FILTER BY SEARCH: [ ]

| ⬍ DATE | ⬍ PATIENT | ⬍ TASK | ⬍ STATUS | | |
|---|---|---|---|---|---|
| FRI 02/23/2007 | | | | | |
| [FRI 02/23/2007 ▽] | 👤 PARKER, SUE | SNV W/ AIDE SUPERVISION | SAVED | 🔗 | ✉ — 40 |
| SAT 03/10/2007 | | | | | |
| [SAT 03/10/2007 ▽] | 👤 PARKER, SUE | SKILLED NURSE VISIT | NOT STARTED | 🔗 | ✉ |
| TUE 09/25/2007 | | | | | |
| [TUE 09/25/2007 ▽] | 👤 SANCHEZ, RAYMOND | PHYSICIAN ORDER | NOT STARTED | | ✉ |
| [TUE 09/25/2007 ▽] | 👤 SANCHEZ, RAYMOND | OASIS-C RESUMPTION OF CARE | SAVED | 🔗 ← 40 | ✉ |
| WED 10/10/2007 | | | | | |
| [WED 10/10/2007 ▽] | 👤 SANCHEZ, RAYMOND | POST HOSPITAL ORDER | NOT STARTED | | ✉ |
| THU 10/11/2007 | | | | | |
| [THU 10/11/2007 ▽] | 👤 ALSDJFA, LADJFALDFJ | PATIENT COMMUNICATION | SAVED | | ✉ |
| THU 10/25/2007 | | | | | |

*FIG. 4*

HEALTHCARE DELIVERY VERIFICATION SYSTEM

CROSS REFERENCE TO RELATED APPLICATIONS

This application claims priority upon and is a continuation of co-pending U.S. Patent Application No. 2014/0278545, Ser. No. 14/205,257, filed on Mar. 11, 2014; which claims priority upon U.S. Provisional Patent Application No. 61/783,913, filed on Mar. 14, 2013. The entire contents of the above applications are incorporated by reference herein.

BACKGROUND

Healthcare is a fundamental need for those living in a modern society. Healthcare agencies assist individuals in maintaining and/or restoring their health, helping them to enjoy a rich and full life. In some cases, it may be necessary to provide healthcare services in the comfort of an individual's home. This may be especially important for those who have reached an advanced age, been injured, or been subjected to surgical procedure(s).

Home healthcare presents its own set of unique management challenges given that the healthcare services are provided at the patient's home instead of at the healthcare professional's office. Specifically, it may be desirable to electronically verify home healthcare visits in order to simplify the verification process, hasten payments to healthcare clinicians and protect against healthcare fraud. As such, there remains a need for a home healthcare management system capable of verifying home healthcare visits in an efficient manner.

SUMMARY

Accordingly, in one embodiment, a system, method and computer readable medium capable of verifying home healthcare visits is described herein. In one embodiment, one or more electronic records concerning a plurality of patients may be stored and made available to clinicians and/or home healthcare agencies. Such records may include personal information concerning the patient, the patient's medical needs and/or upcoming home healthcare visits for each patient.

In one embodiment, the verification process may include a determination of the patient's location as well as a confirmation that the information relating thereto is accurate. In the context of a home healthcare visit, the location where the services are to be rendered may include the patient's home address along with a map and/or directions to the patient's home address.

Once the patient's location has been determined and/or confirmed, the location of the clinician may be determined and compared to the location of the patient. This may involve the use of a Global Positioning System (GPS) enabled smart phone, tablet or other suitable device. In one embodiment, the clinician may be provided with a GPS enabled smart phone, tablet or other suitable device so that his or her location may be determined and compared to the patient's location at or near the time of the scheduled home healthcare visit. A time stamp may be utilized to confirm the location of the clinician at any point in the clinician's work cycle.

The system may also utilize electronic signature data to confirm home healthcare visits. In one embodiment, the system provides one or more signature screens through which the patient may enter his or her electronic signature at any point during the home healthcare visit. The electronic signature may be stored and associated with the electronic record for the patient. The electronic signature may take the form of a digital signature.

In one embodiment, a time stamp may be generated and stored to provide confirmation as to the time that the patient's electronic signature was obtained. Further, stored location information gleaned from the clinician's GPS enabled smartphone, tablet or other suitable device may be cross referenced with the time stamp of the patient signature in order to provide further confirmation that the clinician met with the patient at the proper time and place.

Home healthcare visit verification data stored by the system may be used to generate lists, data tables, reports and/or other documentation for review by interested personnel such as administrators, auditors, surveyors, etc. In one embodiment, the system, method and computer readable medium described herein may be provided as a stand-alone software application or integrated into a proprietary healthcare management software package such as the Kinnser Agency Manager® offered by Kinnser Software, Inc.™

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings; it being understood that the drawings contained herein are not necessarily drawn to scale; wherein:

FIGS. 2-4 are example graphic user interfaces that may be utilized in conjunction with one or more embodiments.

DESCRIPTION

A system, method and computer readable medium capable of managing and verifying healthcare encounters is described herein. In the context of a home healthcare visit, a health care worker (also referred to herein as a clinician) travels to the patient's home and renders one or more healthcare services during the visit. Healthcare services may include any service relating to the wellbeing of the patient, including skilled and non-skilled services, hospice care, etc.

Figure 1:
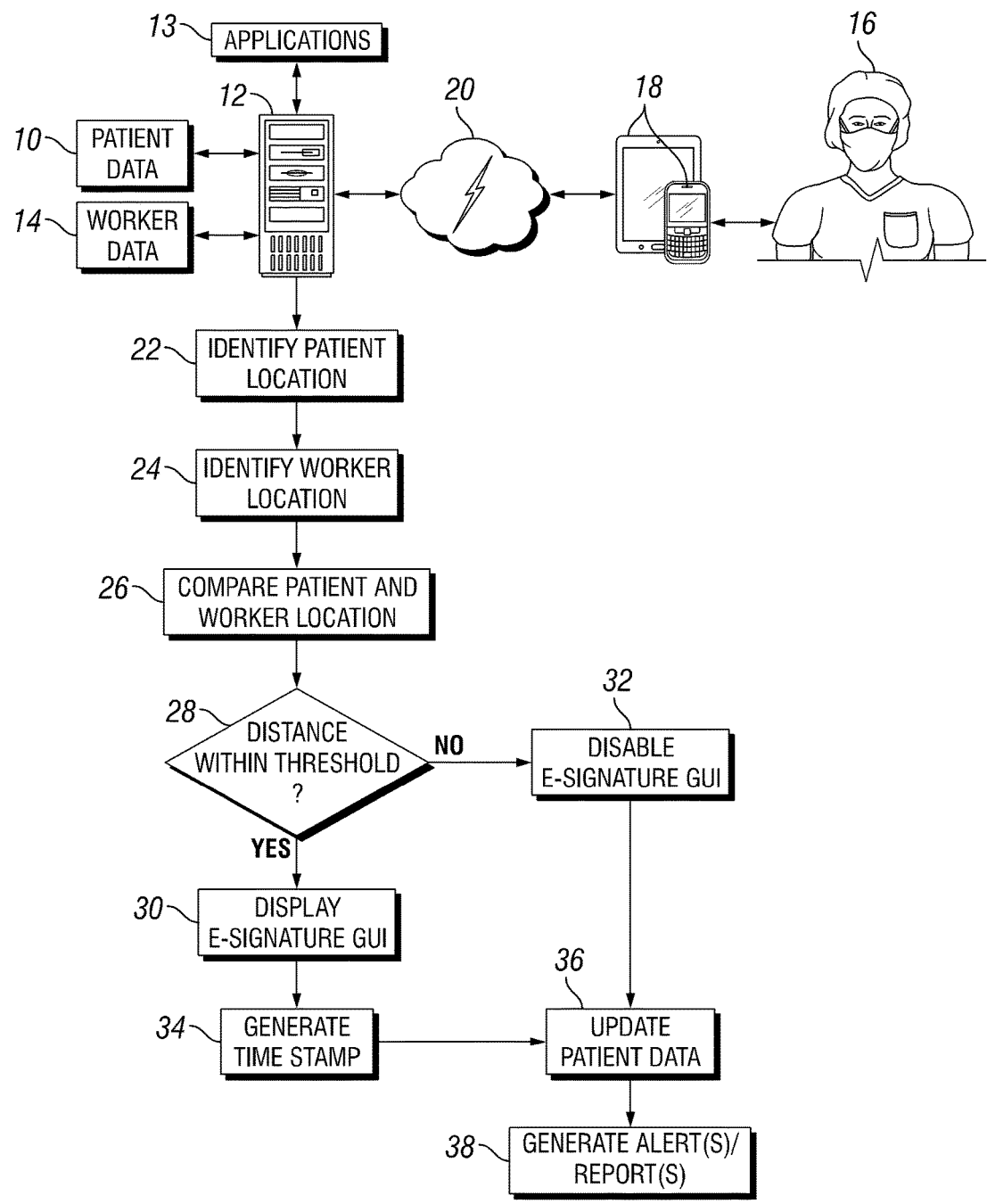
FIG. 1 is a flow chart diagram illustrating a healthcare visit verification process that may be used in conjunction with one or more embodiments.

Referring to FIG. 1, patient data (10) pertaining to a plurality of patients may be stored to a computer system (12) having one or more processor(s), database(s) and/or software Application(s) (13). The computer system may be a server, stand-alone computer system or other suitable processing device.

Patient data may include medical records containing personal information concerning the patient, the patient's medical needs and/or upcoming healthcare visits for each patient. Each record may also include information such as the services to be rendered during a healthcare encounter/visit, the clinician(s) that will render the scheduled services, the location where the services are to be rendered, and/or the date and time of the scheduled visit. In one embodiment, one or more electronic records concerning a plurality of patients may be stored and made available to clinicians.

Healthcare worker data (14) may be stored to the computer system (12). As used herein, a healthcare worker (16) may be any individual assigned with a healthcare related task. Healthcare workers may be employed by an organization, contract workers, temporary workers, part time workers, etc. In one embodiment, each healthcare worker (16) may be provided with an electronic device (18) capable of determining and transmitting its geographical location (and thus the healthcare worker's geographical location) to the computer system (12) via one or more computer networks (20).

In one embodiment, the electronic device (18) may be a laptop, smart phone, tablet or other suitable device. The electronic device may track its location worldwide using triangulation between 3G/4G towers, using GPS, WI-FI or other suitable methodology. The electronic device may also be equipped with one or more software application(s) capable of capturing a location identification as well as a user ID of the healthcare worker associated therewith. Such application(s) may be further capable of displaying data necessary to complete any number of healthcare related tasks, as described in more detail below.

In one embodiment, healthcare worker data may include information such as the geographical location of the worker, the worker's skill, training, and/or experience, the status of the worker, i.e., whether the worker is on-duty, off-duty, working after hours, on vacation, etc., a listing of medical equipment available to the worker and/or in their possession, and/or the transportation available to the worker.

In one embodiment, the system provides electronic visit verification functionality capable of confirming that: (1) the clinician visited the patient at or near the scheduled time and (2) the clinician provided the required healthcare services to the patient. In one embodiment, the verification process may include a determination of the patient's location as well as a confirmation that the information relating thereto is accurate.

Figure 2:
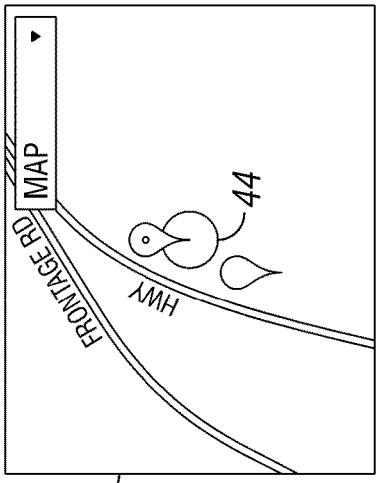

In one embodiment, the patient's location may be identified by accessing the patient's medical record(s) stored by the system, as illustrated by Box (22) of FIG. 1. FIG. 2 illustrates an example graphic user interface (GUI) that may be utilized to provide the healthcare worker with information regarding the patient's location. In the context of a home healthcare visit, the patient's location may be where the services are to be rendered and may include the patient's home address (23A, FIG. 2) along with a map (23B, FIG. 2) illustrating the patient's home address.

Driving directions may also be provided to the clinician in order to help him or her arrive at the patient's home at the scheduled time. The system may utilize a location service, such as Google Maps®. The system may also employ one or more address verification services (such as those provided by the U.S. Postal Service) to confirm that the patient's address is directed to a real-world address.

Once the patient's location has been determined and/or confirmed, the location of the clinician may be determined and compared to the location of the patient, as illustrated by Boxes (24) and (26) of FIG. 1. This may involve the use of a GPS enabled smart phone, tablet or other suitable device. In one embodiment, the clinician may be provided with a GPS enabled smart phone, tablet or other suitable device so that his or her location may be determined and compared to the patient's location at or near the time of the scheduled home healthcare visit.

Figure 3:
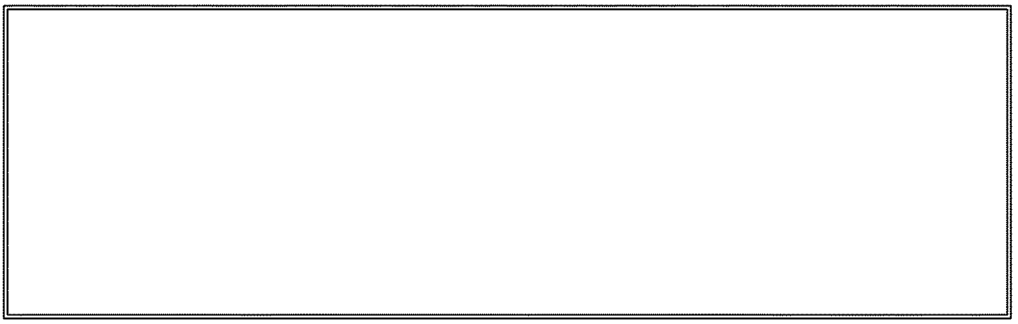

The system may utilize electronic signature data to confirm home healthcare visits. In one embodiment, the system provides a graphic user interface to display one or more signature screens through which the patient may enter his or her electronic signature at any point during the home healthcare visit. FIG. 3 illustrates an example signature screen that may be utilized in conjunction with one or more embodiments.

In one embodiment, the electronic signature of the patient may be obtained at the conclusion of the visit in order to provide confirmation that the clinician provided the required home healthcare services to the satisfaction of the patient. The electronic signature may be stored and associated with the electronic record for the patient. The electronic signature may take the form of a digital signature. In one embodiment, the system may provide a check box or other functionality (27, FIG. 3) to indicate circumstances where the patient was unable or unwilling to provide an electronic signature.

In one embodiment, the comparison of the patient's location and the healthcare worker's location may be utilized in order to determine the geographical distance between the patient and the worker. This distance value may be utilized by the system in order to enable/disable the electronic signature screen where appropriate. For example, if a distance threshold value of 100 meters has been entered (or set by default by the system), the system may check to see if the calculated distance value between the patient and the clinician is equal to or less than the 100 meters, as illustrated by Box (28) of FIG. 1.

If the distance value falls inside the threshold value, i.e., is equal to or less than 100 meters, the electronic signature screen may be enabled and displayed upon the clinician's device, as illustrated by Box (30). The patient may then enter his or her e-signature into the space on the graphic user interface provided on the clinician's device and the signature may be stored by the system. In this example, a calculated distance value outside the threshold value, i.e., greater than 100 meters, may result in the electronic signature screen being disabled, as illustrated by Box (32) of FIG. 1.

In one embodiment, a time stamp may be generated at or near the time when the patient's e-signature is obtained by the system, as illustrated by Box (34) of FIG. 1. In this example, the time stamp provides further confirmation as to the time that the patient's electronic signature was obtained. Further, stored location information gleaned from the clinician's GPS enabled smartphone, tablet or other suitable device may be cross referenced with the time stamp of the patient signature in order to provide further confirmation that the clinician met with the patient at the proper time and place. The time stamp may also be utilized to indicate when the electronic signature screen was enabled or disabled, depending on the circumstances.

Clinician location data may be recorded and stored throughout the day (or any other suitable time period) to ensure that the clinician visits each patient at the proper time and place. A time stamp may be utilized to confirm the location of the clinician at any point in the clinician's work cycle.

Upon receipt (or non-receipt) of an electronic signature, the system may update the patient's medical record to indicate the status of the medical visit in question, as illustrated by Box (36) of FIG. 1. In this example, receipt of the patient's e-signature at or near the patient's location provides verification that the health care visit took place. Further, alert(s) and/or report(s) regarding the healthcare visit may be generated and provided to authorized personnel, as illustrated by Box (38) of FIG. 1 and as described further below.

In one embodiment, the system provides one or more graphic user interfaces through which authorized personnel may enter distance threshold values for use during the verification process. Authorized personnel may also utilize the graphic user interface to pick and choose which home healthcare visits will require verification and/or may disable electronic visit verification functionality for selected healthcare visits, healthcare workers and/or patients. Further, authorized personnel may toggle the map, geo-location and driving direction features on and off for individual healthcare visits, clinicians, and/or patients as they see fit.

A stylus, touch screen or other suitable device may be utilized to obtain the patient's signature. An image and/or video capture feature may also be utilized such that a picture and/or video of the patient is collected at the conclusion of the visit, when he or she signs the electronic verification and/or when the e-signature screen is enabled or disabled. This feature, along with the time stamp, provides further proof that the clinician met with the patient and provided the required healthcare services to the satisfaction of the patient. This feature may be especially helpful in circumstances where the patient is unable or unwilling to sign, thus providing proof that the clinician visited with the patient even though an electronic signature was not obtained.

In one embodiment, an audio capture feature may be utilized to enable audio recording at the conclusion of the visit, when the patient signs the electronic verification and/or when the e-signature screen is enabled or disabled. In this example, an event, such as the disabling of the e-signature screen by the system, would trigger an automatic audio recording feature on the healthcare worker's electronic device. In this example, the audio recording would provide additional information regarding the circumstances surrounding the collection (or non-collection) of the e-signature from the patient.

The system may also provide status information regarding which home healthcare visits have been verified. Graphical indications, textual indications and/or various color schemes may be utilized to present status information to authorized personnel. For example, one or more icon(s) may be presented on the clinician's "to do list" to indicate whether a particular visit has been verified or not.

FIG. 4 illustrates an example "to do list" that may be utilized in conjunction with one or more embodiments. The icon(s) (40, FIG. 4) may also be linked with one or more electronic signature screens so that the user need only click on the appropriate icon(s) in order to bring up the signature screen for the patient during the course of a home healthcare visit.

In one embodiment, an icon in the shape of a house may be utilized in order to quickly convey verification status information to authorized personnel via one or more graphic user interfaces. For example, an empty house icon may be utilized to represent a healthcare visit/task that has not been verified while a house icon having a superimposed checkmark may be utilized to represent a healthcare visit that has been verified by an electronic signature and/or a time stamp as described above. Further, verified visits may be color coded with a green color (for example) while un-verified visits may be color coded with a red color (for example), etc.

In one embodiment, one or more verification icons may be included in payroll, invoicing, therapy management, administration and/or other suitable graphic user interfaces (through Kinnser Agency Manager® for example) in order to make the verification information provided by the system accessible to authorized personnel. For example, a verification icon may be provided next to verified healthcare visits in order to indicate that the healthcare visit/task is ready to be run for payroll.

In one embodiment, the system may identify/determine a geographic code associated with the patient's location and compare it to a geographic code associated with the clinician's device at the time of the patient's electronic signature. The time stamp of the electronic signature may also be compared to the scheduled visit time/date in order to confirm whether the patient signature corresponds to the scheduled visit time frame.

This feature allows home health administrators, auditors, surveyors and other interested personnel to verify home healthcare visits using electronically stored location and/or timestamp information, reducing the amount of time required to manually verify patient visits. Further, verification information may be incorporated into payroll/invoice request forms and/or integrated into payroll/invoice records in order to hasten payment processing.

In one embodiment, the system may provide accuracy data pertaining to the location of the patient and/or the clinician. Accuracy information may include real time indication(s) that GPS is "unavailable" or that the system is "waiting to receive" geographical information from the location service. Further, if location information has been received by the system, accuracy information (42, FIG. 2) may include the system's level of confidence in the location data. For example, status messages such as "location>1000 meters," "location between 1000 meters and 300 meters," or "location within 300 meters" may be provided upon the clinician's graphical user interface and/or other display hardware.

Graphical indications, textual indications and/or various color schemes may be utilized as well. For example, the system may provide a circle (44, FIG. 2) around the clinician's location on a map of the geographical area in order to indicate the level of confidence, e.g., within 300 meters, of the location data. An option to refresh location data may also be provided.

Data gleaned from the comparison of the patient's location and the clinician's location at the time of the patient's signature may be provided in real time to the clinician or other personnel and/or stored for later analysis. This may be accomplished using a graphic or textual display indicating the results of the comparison. For example, the system may indicate that the difference between the patient's location and the clinician's location, as determined by the system, is 500 meters plus or minus 200 meters. In this example, 500 meters would be the geographical difference between the patient's location and the clinician's location and 200 meters would be the level of confidence in the location data. This information may be displayed using graphical indications, textual indications and/or various color schemes.

A threshold accuracy and/or comparison level may be defined by the system and/or entered by authorized personnel. The threshold accuracy and/or comparison level may be utilized to decide what level of accuracy and/or confidence is required in order to complete the home health visit verification process. In one embodiment, if the level of accuracy and/or the level of confidence if not met, the electronic signature screen may be disabled.

Consider an example where a threshold accuracy level is set to be 1000 meters. In this example, the system would not allow the patient's signature to be obtained, i.e., the signature screen may be disabled, if the accuracy is determined to be a value greater than 1000 meters. Likewise, in this example, if a threshold comparison level is set to be 500 meters, the system would not allow the patient's signature to be obtained if the comparison of the patient's location and the clinician's location generates a distance value greater than 500 meters. In one embodiment, this feature may be enabled and/or disabled by authorized personnel as needed.

Home healthcare visit verification data stored by the system may be used to generate lists, data tables, reports and/or other documentation for review by interested personnel such as administrators, auditors, surveyors, etc. In one embodiment, a geographic deviation report may be generated by the system. A geographic deviation report may show all of the visits for all clinicians from an agency over a period that the user chooses (e.g. the past week). The report may show all patients, each visit to each patient, the clinician that made each visit, and whether each visit was verified using electronic home healthcare visit verification. The report may also include a setting to illustrate not only visits that were verified, but that happened more than "n" number of meters (or feet, yards, miles, etc.) away from the patient's address on file.

In one embodiment, the geographic deviation report allows a manager or auditor at a home healthcare agency to sort all the visits for a particular timeframe and find any that fall out of a predefined distance value. This feature allows the manager or other authorized personnel to "drill down" and look at more detail for these visits by sorting the visits by verification status. Such visits might have been performed somewhere other than the patient's address (e.g. a skilled nurse facility, family members home, etc.) or perhaps the system has access to the patient's signature but not a geographic code (because for example, location services were not available), or perhaps they were fraudulent visits.

A geography deviation alert may also be provided by the system. This feature may be utilized in much the same way as the geography deviation report described above, but provides a real-time message/alert to the clinician or other authorized personnel during the visit. For example, if a manager employs a clinician that he or she is having timeliness issues with (or suspected honesty issues), the manager may decide to set up deviation alerts for visits done by the clinician in question. If a visit is scheduled to be at the home of a patient and a visit verification is submitted, but the clinician's location is outside the threshold range set by the manager, an email, text message, or other alert may be triggered and provided to the clinician.

In one embodiment, the system allows a home healthcare visit to be verified without the intervention of the clinician. This may be accomplished by generating and storing a time stamp when the clinician carries his or her GPS enabled smartphone, tablet or other suitable device through a ring or "geo-fence" located around the patient's residence. In one embodiment, authorized personnel may be given the option to set a global radius (fence) value around the patient's address and/or the radius value may be set to a default value by the system. The applicable geo-fence radius may be illustrated on a graphic user interface around the patient's address using a circle or other identifier.

In one embodiment, the fence value may utilize the geo-location settings of the healthcare worker's electronic device to detect when a clinician is close enough to the patient's address in order to "check in." For example, the system may ping the clinician's electronic device to determine if the clinician is inside the patient's defined radius. If the clinician is inside the clinician's geo-fence radius, the application may track and record a "time in" time stamp for the visit. Another time stamp may then be generated and stored when the clinician leaves the patient's residence, thus carrying his or her GPS enabled smartphone, tablet or other suitable device through the ring or geo-fence located around the patient's residence. Thus, when the clinician leaves the pre-set radius, the system may track the time the clinician left and use this time stamp as a "time out" for the visit.

In one embodiment, the software may direct the clinician's device to emit an audible alert to bring the "time in" and "time out" events to the attention of the clinician as they happen. The alert may also request that the clinician provide verification on the screen of their device, e.g., "Yes, I was at 123 Main street from 8:30 a.m. to 9:15 a.m. on Jun. 1, 2013."

In one embodiment, the clinician may manually "check in" and "check out" using one or more buttons provided by a graphic user interface. For example, the user may click a button, such as a "Start Visit" button, in order to activate a timer when he or she arrives at the patient's residence. When the clinician leaves the patient's residence, they may click a button, such as a "Finish Visit" button to discontinue the timer. This feature may be used in conjunction with one or more of the verification comparisons described above.

In one embodiment, the system may also provide check-in and/or check-out reminders. For example, an audio alert may be generated in order to remind the clinician to manually enter their check-in or check-out times. Such alerts may be triggered off schedule time (e.g. appointment is for 1:00 pm-2:00 pm and the chime/message alert goes off at 12:55 pm and 1:55 pm, respectively) or may be utilized using a "geo-fence" as described above. For example, when a clinician gets within 50 meters (or any desired value) of the address they are supposed to be visiting, the chime and message alert may be activated on their device to remind the clinician to check in or out.

Some home healthcare visits may require that a clinician be at the appointed address at a particular time (e.g. "private duty" visits where the customer has more control over scheduling vs. a Medicare paid nurse visit where the Agency/nurse has control over the schedule). In this example, the system may send an alert to a set of subscribers when the clinician crosses the threshold of the "geo-fence" (as described above) generating an "in" event, or when the electronic signature/submit process is triggered by the software.

In this example, subscribers may include home healthcare agencies (including specific managers or schedulers that want to know that the clinician arrives on time) and/or family members of the patient that might want to be notified that a clinician has arrived. Alerts may be provided using any suitable convention, including emails, text messages, voicemail messages, etc.

In one embodiment, a "visit within schedule" feature may also be provided. This feature may be used to verify that a visit took place within a desired time frame. In one embodiment, this may be accomplished by determining if the clinician visited the patient's residence within a scheduled window of time, i.e., between 10:00 am and 11:00 am on Wednesday or within a threshold time range. Specifically, if the electronic signature and geo-code stamp are taken and fall within the 10:00 am-11:00 am timeframe, the visit would be recorded as a "time within scheduled visit" occurrence.

In one embodiment, the elapsed time of a visit may be calculated from automatic or manual check-in and check-out times recorded by the system in order to indicate the total time that a clinician was at the patient's address. The calculated values may be used to generate report(s) and/or visual view(s) illustrating which home healthcare visits occurred during the scheduled time periods.

In one embodiment, the system, method and computer readable medium described herein may be provided as a stand-alone software application or integrated into a proprietary healthcare management software package such as the Kinnser Agency Manager® offered by Kinnser Software, Inc.™ In one embodiment, electronic visit verification functionality may be integrated into the "to do list" (also referred to as a "hotbox"), clinical form, episode manager task list, therapy manager, and/or payroll manager screens provided by the Kinnser Agency Manager® software package.

The methods described herein may be implemented on any suitable computer system capable of processing electronic data. Computer system(s), may run programs containing instructions, that, when executed, perform methods according to the principles described herein. Furthermore, the methods described herein may be fully automated and able to operate continuously, as desired.

The computer system may utilize one or more central processing units, memory, communications or I/O modules, graphics devices, and mass storage devices such as tapes and discs. Storage device may include a floppy drive, hard drive, CD-ROM, optical drive, or any other form of storage device. In addition, the storage devices may be capable of receiving a floppy disk, CD-ROM, DVD-ROM, disk, flash drive or any other form of computer-readable medium that may contain computer-executable instructions. Further communication devices may be a modem, network card, or any other device to enable communication to receive and/or transmit data. It should be understood that the computer system may include a plurality of interconnected (whether by intranet or Internet) computer systems, including without limitation, personal computers, mainframes, PDAs, cell phones and the like.

It should be understood that the various technologies described herein may be implemented in connection with hardware, software or a combination of both. Thus, various technologies, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the various technologies.

In the case of program code execution on programmable computers, the computing device may include a processor, a storage medium readable by the processor (including volatile and non-volatile memory and/or storage elements), at least one input device, and at least one output device. One or more programs that may implement or utilize the various technologies described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

The computer system may include hardware capable of executing machine readable instructions, as well as the software for executing acts that produce a desired result. In addition, computer system may include hybrids of hardware and software, as well as computer sub-systems.

Hardware may include at least processor-capable platforms, such as client-machines (also known as personal computers or servers), and hand-held processing devices (such as smart phones, personal digital assistants (PDAs), or personal computing devices (PCDs), for example). Further, hardware may include any physical device that is capable of storing machine-readable instructions, such as memory or other data storage devices. Other forms of hardware include hardware sub-systems, including transfer devices such as modems, modem cards, ports, and port cards, for example.

Software includes any machine code stored in any memory medium, such as RAM or ROM, and machine code stored on other devices (such as floppy disks, flash memory, or a CD ROM, for example). Software may include source or object code, for example. In addition, software encompasses any set of instructions capable of being executed in a client machine or server.

A database may be any standard or proprietary database software, such as Oracle, Microsoft Access, SyBase, or DBase II, for example. The database may have fields, records, data, and other database elements that may be associated through database specific software. Additionally, data may be mapped. Mapping is the process of associating one data entry with another data entry. For example, the data contained in the location of a character file can be mapped to a field in a second table. The physical location of the database is not limiting, and the database may be distributed. For example, the database may exist remotely from the server, and run on a separate platform.

Further, the computer system may operate in a networked environment using logical connections to one or more remote computers. The logical connections may be any connection that is commonplace in offices, enterprise-wide computer networks, intranets, and the Internet, such as local area network (LAN) and a wide area network (WAN). The remote computers may each include one or more application programs.

When using a LAN networking environment, the computer system may be connected to the local network through a network interface or adapter. When used in a WAN networking environment, the computer system may include a modem, wireless router or other means for establishing communication over a wide area network, such as the Internet. The modem, which may be internal or external, may be connected to the system bus via the serial port interface. In a networked environment, program modules depicted relative to the computer system, or portions thereof, may be stored in a remote memory storage device.

Although the invention has been described with reference to specific embodiments, this description is not meant to be construed in a limited sense. Various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention.

What is claimed is:

1. A computer implemented method for verifying a healthcare encounter comprising:
one or more computer processors for:
determining a home address of a patient for a healthcare visit;
determining a geographical location of an electronic device associated with a healthcare worker assigned to provide healthcare to the patient at the patient's home address at a given time;
enabling an electronic signature screen upon the healthcare worker's electronic device if the geographical location of the healthcare worker's electronic device is within a threshold distance of the patient's home address at the given time;
receiving the patient's electronic signature upon the electronic signature screen in order to verify that the healthcare visit took place; wherein the electronic signature screen is disabled if the geographical location of the healthcare worker's electronic device is not within a threshold distance of the patient's home address at the given time such that the healthcare visit cannot be verified; and verifying the home address of the patient prior to disabling or enabling the electronic signature screen.

2. The method of claim 1, further comprising:

generating a map illustrating the geographical location of the patient's home address and displaying the map upon the healthcare worker's electronic device.

3. The method of claim 1, further comprising:

generating driving directions to the patient's home address and displaying the driving directions upon the healthcare worker's electronic device.

4. The method of claim 1, further comprising:

generating a geographic deviation alert.

5. The method of claim 4, further comprising:

transmitting the geographic deviation alert to one or more interested parties.

6. The method of claim 1, further comprising:

displaying healthcare task completion data upon the healthcare worker's electronic device.

7. The method of claim 1, further comprising:

displaying a checkbox upon the healthcare worker's electronic device to indicate a situation where the patient is unwilling or unable to sign the electronic signature screen.

8. A computer system for verifying a healthcare encounter comprising:

a computer processor operative to:
  determine a home address of a patient for a healthcare visit;
  determine a geographical location of an electronic device associated with a healthcare worker assigned to provide healthcare to the patient at the patient's home address at a given time;
  enable an electronic signature screen upon the healthcare worker's electronic device if the geographical location of the healthcare worker's electronic device is within a threshold distance of the patient's home address at the given time;
  receive the patient's electronic signature upon the electronic signature screen in order to verify that the healthcare visit took place; wherein the electronic signature screen is disabled if the geographical location of the healthcare worker's electronic device is not within a threshold distance of the patient's home address at the given time such that the healthcare visit cannot be verified;
  generate a verification alert indicating whether the healthcare visit has or has not been verified; and
  transmit the verification alert to one or more interested parties.

9. The system of claim 8, wherein the processor is operative to:

determine an accuracy level associated with the geographical location of the healthcare worker's electronic device.

10. The system of claim 9, wherein the processor is operative to:

display the accuracy level upon the healthcare worker's electronic device.

11. The system of claim 9, wherein the processor is operative to:

apply an accuracy level threshold to the geographical location of the healthcare worker's electronic device prior to disabling or enabling the electronic signature screen.

12. The system of claim 8, wherein the processor is operative to:

determine a level of confidence associated with the geographical location of the healthcare worker's electronic device.

13. The system of claim 12, wherein the processor is operative to:

display the level of confidence upon the healthcare worker's electronic device.

14. The system of claim 12, wherein the processor is operative to:

apply a level of confidence threshold to the geographical location of the healthcare worker's electronic device prior to disabling or enabling the electronic signature screen.

15. A non-transitory computer-readable storage medium for verifying a healthcare encounter comprising instructions which, when executed, cause a computing device to:

determine a home address of a patient for a healthcare visit;

determine a geographical location of an electronic device associated with a healthcare worker assigned to provide healthcare to the patient at the patient's home address at a given time;

enable an electronic signature screen upon the healthcare worker's electronic device if the geographical location of the healthcare worker's electronic device is within a threshold distance of the patient's home address at the given time;

receive the patient's electronic signature upon the electronic signature screen in order to verify that the healthcare visit took place; wherein the electronic signature screen is disabled if the geographical location of the healthcare worker's electronic device is not within a threshold distance of the patient's home address at the given time such that the healthcare visit cannot be verified; and provide a graphic user interface for receiving selections regarding which healthcare visits will require verification and for displaying which healthcare visits have or have not been verified.

16. The computer readable medium of claim 15, wherein the instructions, when executed, cause the computing device to:

display a verification icon indicating whether the healthcare visit has or has not been verified.

17. The computer readable medium of claim 16, wherein the verification icon further comprises a house shaped graphic.

18. The computer readable medium of claim 16, wherein the verification icon is linked to the electronic signature screen.

19. The computer readable medium of claim 15, wherein a geo-fence is utilized to determine whether the geographical location of the healthcare worker's electronic device is within the threshold distance of the patient's home address at the given time.

20. The computer readable medium of claim 19, wherein the instructions, when executed, cause the computing device to:

generate a geo-fence alert when the healthcare worker's electronic device crosses a geo-fence boundary located around the patient's home address; and transmit the geo-fence alert to one or more interested parties.

* * * * *